(12) United States Patent
Wood et al.

(10) Patent No.: US 10,828,125 B2
(45) Date of Patent: Nov. 10, 2020

(54) DUAL ZOOM AND DUAL FIELD-OF-VIEW MICROSCOPE

(71) Applicants: Michael Frank Gunter Wood, Toronto (CA); Cameron Anthony Piron, Toronto (CA); Tammy Kee-Wai Lee, Toronto (CA); Kamyar Abhari, Toronto (CA); Kai Michael Hynna, Toronto (CA)

(72) Inventors: Michael Frank Gunter Wood, Toronto (CA); Cameron Anthony Piron, Toronto (CA); Tammy Kee-Wai Lee, Toronto (CA); Kamyar Abhari, Toronto (CA); Kai Michael Hynna, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/580,323

(22) PCT Filed: Nov. 3, 2015

(86) PCT No.: PCT/CA2015/051128
§ 371 (c)(1),
(2) Date: Dec. 7, 2017

(87) PCT Pub. No.: WO2017/075687
PCT Pub. Date: May 11, 2017

(65) Prior Publication Data
US 2018/0168769 A1 Jun. 21, 2018

(51) Int. Cl.
*A61B 1/045* (2006.01)
*A61B 90/00* (2016.01)
(Continued)

(52) U.S. Cl.
CPC ........ *A61B 90/361* (2016.02); *A61B 1/00188* (2013.01); *A61B 1/00193* (2013.01);
(Continued)

(58) Field of Classification Search
CPC ....... A61B 90/361; A61B 90/30; A61B 90/37; A61B 34/20
See application file for complete search history.

(56) References Cited

U.S. PATENT DOCUMENTS 6,006,126 A * 12/1999 Cosman ................ A61B 34/20
600/414
6,118,475 A * 9/2000 Iijima ..................... G01C 11/06
348/42
(Continued)

*Primary Examiner* — Joanne M Hoffman
(74) *Attorney, Agent, or Firm* — Ridout & Maybee LLP

(57) ABSTRACT

A surgical imaging system is described. The system includes first and second optical assemblies. Each optical assembly defines a respective optical axis, and each includes a respective set of one or more optics for adjusting field-of-view (FOV) and focus and a respective camera for capturing an image. The system includes a controller for controlling the optical assemblies and for switching the surgical imaging system between a coupled configuration and an uncoupled configuration. In the coupled configuration, the first optical assemblies are controlled to adjust the respective sets of optics and/or the respective optical axes in dependence on each other. In the uncoupled configuration, the optical assemblies are controlled to adjust the respective sets of optics, and the respective optical axes independently of each other.

21 Claims, 9 Drawing Sheets

(51) Int. Cl.
*A61B 90/20* (2016.01)
*A61B 1/00* (2006.01)
*A61B 34/20* (2016.01)
*A61B 90/30* (2016.01)
*A61B 90/14* (2016.01)

(52) U.S. Cl.
CPC .............. *A61B 1/045* (2013.01); *A61B 34/20* (2016.02); *A61B 90/20* (2016.02); *A61B 90/30* (2016.02); *A61B 90/37* (2016.02); *A61B 90/14* (2016.02); *A61B 90/39* (2016.02); *A61B 2034/2051* (2016.02); *A61B 2034/2055* (2016.02); *A61B 2090/306* (2016.02); *A61B 2090/365* (2016.02); *A61B 2090/367* (2016.02); *A61B 2090/371* (2016.02); *A61B 2090/374* (2016.02); *A61B 2090/376* (2016.02); *A61B 2090/378* (2016.02); *A61B 2090/3735* (2016.02); *A61B 2090/3762* (2016.02)

(56) References Cited

U.S. PATENT DOCUMENTS

| | | | | |
|---|---|---|---|---|
| 6,507,359 B1* | 1/2003 | Muramoto | ............ | H04N 5/772 345/8 |
| 6,643,396 B1* | 11/2003 | Hendriks | ............... | G01C 11/06 250/559.23 |
| 6,675,040 B1* | 1/2004 | Cosman | ............ | G06T 3/00 600/427 |
| 6,690,413 B1* | 2/2004 | Moore | ............ | B60R 1/00 348/148 |
| 6,701,081 B1* | 3/2004 | Dwyer | ............ | G03B 41/00 396/329 |
| 7,272,306 B2* | 9/2007 | Zhang | ............ | B25J 9/1697 348/159 |
| 7,411,739 B2* | 8/2008 | Obrebski | ............ | G02B 3/14 349/200 |
| 7,486,815 B2* | 2/2009 | Kristjansson | ............ | G06K 9/32 348/169 |
| 7,561,733 B2* | 7/2009 | Vilsmeier | ............ | A61B 5/103 382/128 |
| 7,623,250 B2* | 11/2009 | Moctezuma de la Barrera | .......... | G01S 5/163 356/604 |
| 7,948,515 B1* | 5/2011 | Hines | ............ | G03B 35/08 348/47 |
| 8,105,233 B2* | 1/2012 | Abou El Kheir | .... | A61B 1/0008 348/47 |
| 9,070,222 B2* | 6/2015 | McNally | ............ | G06T 19/006 |
| 9,314,305 B2* | 4/2016 | Jenkins | ............ | G01R 33/286 |
| 9,545,188 B2* | 1/2017 | Jessop | ............ | A61B 1/00188 |
| 9,687,307 B2* | 6/2017 | Wu | ............ | A61B 5/064 |
| 10,021,351 B2* | 7/2018 | Jessop | ............ | H04N 7/18 |
| 2002/0163499 A1* | 11/2002 | Sauer | ............ | H04N 13/004 345/156 |
| 2004/0017607 A1* | 1/2004 | Hauger | ............ | G02B 21/22 359/376 |
| 2007/0156017 A1* | 7/2007 | Lamprecht | ......... | A61B 1/00193 600/102 |
| 2008/0004533 A1* | 1/2008 | Jansen | ............ | A61B 5/0059 600/476 |
| 2008/0117287 A1* | 5/2008 | Park | ............ | H04N 7/18 348/36 |
| 2008/0218588 A1* | 9/2008 | Stetten | ............ | A61B 8/0833 348/47 |
| 2010/0026789 A1* | 2/2010 | Balogh | ............ | A61B 6/022 348/50 |
| 2010/0295926 A1* | 11/2010 | Estrada | ............ | G06T 7/85 348/47 |
| 2011/0243546 A1* | 10/2011 | Pace | ............ | H04N 5/2251 396/428 |
| 2012/0113232 A1* | 5/2012 | Joblove | ............ | H04N 13/0242 348/48 |
| 2012/0140044 A1* | 6/2012 | Galstian | ............ | A61B 1/00193 348/47 |
| 2013/0002815 A1* | 1/2013 | Smoot | ............ | G06T 19/006 348/43 |
| 2013/0010081 A1* | 1/2013 | Tenney | ............ | G05B 19/4086 348/47 |
| 2013/0041215 A1* | 2/2013 | McDowall | ............ | G02B 27/283 600/109 |
| 2013/0041216 A1* | 2/2013 | McDowall | ............ | G02B 5/04 600/109 |
| 2013/0041226 A1* | 2/2013 | McDowall | ............ | A61B 1/00009 600/166 |
| 2013/0041267 A1* | 2/2013 | Ntziachristos | ..... | A61B 1/00009 600/476 |
| 2013/0211588 A1* | 8/2013 | Diolaiti | ............ | B25J 9/1689 700/249 |
| 2013/0222376 A1* | 8/2013 | Shimazaki | ......... | G02B 27/2228 345/419 |
| 2013/0235163 A1* | 9/2013 | Joo | ............ | H04N 13/007 348/47 |
| 2014/0163736 A1* | 6/2014 | Azizian | ............ | A61B 19/2203 700/259 |
| 2014/0240457 A1* | 8/2014 | Xia | ............ | H04N 13/0239 348/43 |
| 2015/0018622 A1* | 1/2015 | Tesar | ............ | A61B 1/05 600/202 |
| 2015/0077575 A1* | 3/2015 | Krig | ............ | H04N 1/00204 348/207.11 |
| 2015/0085095 A1* | 3/2015 | Tesar | ............ | A61B 1/005 348/77 |
| 2015/0156461 A1* | 6/2015 | Jessop | ............ | H04N 7/18 348/47 |
| 2016/0015258 A1* | 1/2016 | Levin | ............ | A61B 1/00006 600/109 |
| 2016/0147131 A1* | 5/2016 | Richards | ............ | G03B 13/36 348/187 |
| 2016/0358332 A1* | 12/2016 | Watanabe | ............ | G06T 7/0012 |
| 2016/0360121 A1* | 12/2016 | Cheng | ............ | H04N 13/0239 |
| 2017/0205612 A1* | 7/2017 | Carloni | ............ | G02B 21/0008 |

* cited by examiner

DUAL ZOOM AND DUAL FIELD-OF-VIEW MICROSCOPE

FIELD

The present disclosure relates to microscopes having dual zoom optics and dual field-of-view imaging. Such a microscope may be used during image guided medical procedures.

BACKGROUND

Surgical microscopes are often used during surgical procedures to provide a detailed or magnified view of the surgical site during a medical procedure. Single-channel imaging systems typically do not provide stereoscopic video images, however single-channel microscopes may be preferable to stereoscopic microscopes for certain functions. The need to switch between different microscopes during a medical procedure may be time-consuming, frustrating for the surgeon and/or difficult in the limited space provided by the operating theatre.

Further, there is currently no simple way to provide a surgeon with two different fields of view (e.g., a zoomed-in micro view and a less magnified macro view) at the same time. This may make it difficult for the surgeon to obtain contextual information about a zoomed-in view.

SUMMARY

In some examples, the present disclosure describes a surgical imaging system. The system includes: a first optical assembly defining a first optical axis, the first optical assembly comprising: a first set of one or more optics for adjusting a first field-of-view (FOV) and a first focus; and a first camera for capturing a first image of the first FOV; a second optical assembly defining a second optical axis, the second optical assembly comprising: a second set of one or more optics for adjusting a second FOV and a second focus; and a second camera for capturing a second image of the second FOV; and a controller for controlling the first and the second optical assemblies and for switching the surgical imaging system between a coupled configuration and an uncoupled configuration; wherein, in the coupled configuration, the first and the second optical assemblies are controlled to adjust the respective first and second sets of optics and/or the respective first and second optical axes in dependence on each other; wherein, in the uncoupled configuration, the first and the second optical assemblies are controlled to adjust the respective first and second sets of optics, and the respective first and second optical axes independently of each other.

In some examples, the present disclosure describes a processor for controlling the surgical imaging system disclosed herein. The processor is configured to: provide a user interface to receive control input, via an input device coupled to the processor, for controlling the optical imaging system; transmit control instructions to the controller of the optical imaging system to adjust the respective first and second sets of optics and/or the respective first and second optical axes in accordance with the control input; and receive image data from the first and second cameras for outputting to an output device coupled to the processor.

In some examples, the present disclosure describes a system for imaging a surgical site during a surgical procedure. The system includes: the surgical imaging system disclosed herein; a display for displaying images received from each of the first and second cameras; and a medical navigation system for tracking a target object during the surgical procedure; wherein the controller of the surgical imaging system is configured to adjust the surgical imaging system based on tracking of the target object.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
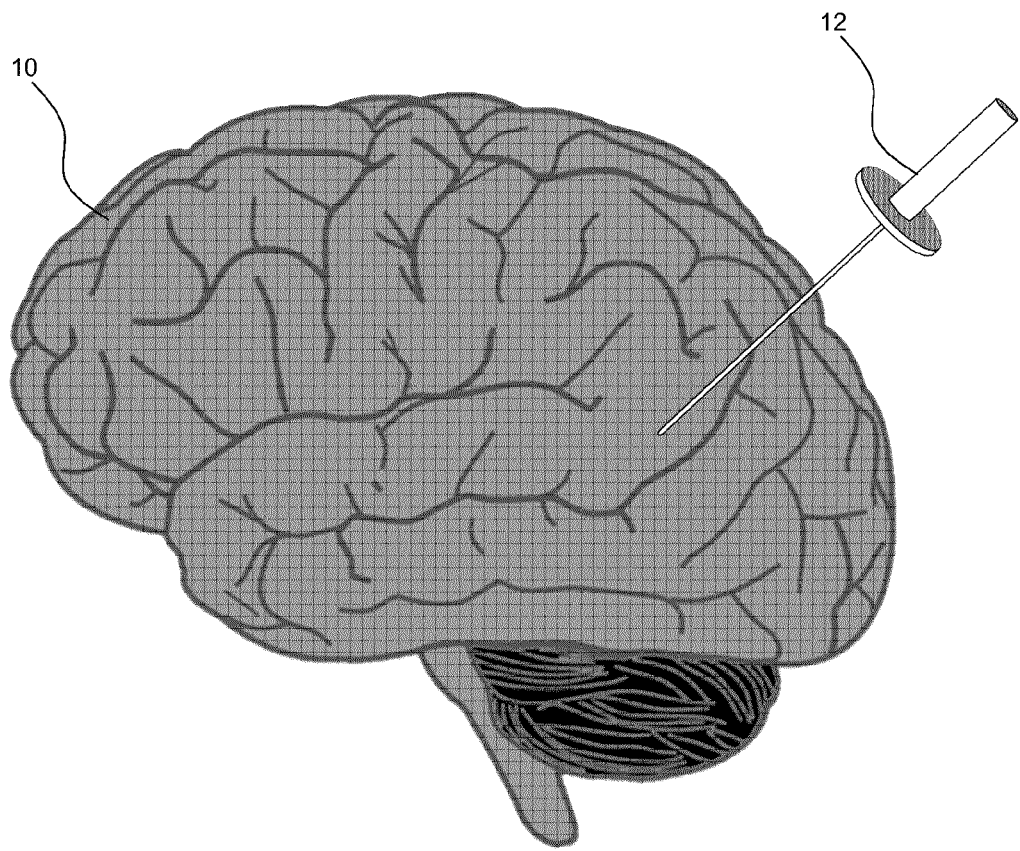
FIG. 1 illustrates the insertion of an access port into a human brain, for providing access to internal brain tissue during an example medical procedure.

In various examples, the present disclosure describes an example imaging system that may help to address some of the challenges discussed above. For example, the disclosed imaging system may enable a user (e.g., a surgeon) to obtain 3D views, high magnification narrow field views, and wide field views without having to switch between separate imaging systems. Further, the disclosed imaging system may provide dual fields-of-view (FOVs), in which narrow field and wide field views are simultaneously viewable. Using examples of the imaging system described herein, a surgeon may change between different viewing modes mid-surgery, for example switching to a 3D view when needed for depth perception (e.g., to perform complex vascular work), and switching to dual FOVs for situations where high magnification and situational context is desired (e.g., for suturing).

The systems and methods described herein may be useful in the field of neurosurgery, including oncological care, neurodegenerative disease, stroke, brain trauma and orthopedic surgery. The teachings of the present disclosure may be applicable to other conditions or fields of medicine. It should be noted that while the present disclosure describes examples in the context of neurosurgery, the present disclosure may be applicable to other surgical procedures that may use intraoperative optical imaging.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not part of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" may be understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest without having to spend excessive amounts of time and concentration repositioning tools, scopes and/or cameras during the medical procedure.

FIG. 1 illustrates the insertion of an access port into a human brain, for providing access to internal brain tissue during a medical procedure. In FIG. 1, an access port 12 is inserted into a human brain 10, providing access to internal brain tissue. The access port 12 may include such instruments as catheters, surgical probes, or cylindrical ports such as the NICO BrainPath™. Surgical tools and instruments may then be inserted within the lumen of the access port 12 in order to perform surgical, diagnostic or therapeutic procedures, such as resecting tumors as necessary. In the example of a port-based surgery, a straight or linear access port 12 is typically guided down a sulci path of the brain. Surgical instruments would then be inserted down the access port 12.

The present disclosure applies equally well to catheters, deep brain stimulation (DBS) needles, a biopsy procedure, and also to biopsies and/or catheters in other medical procedures performed on other parts of the body, as well as to medical procedures that do not use an access port. Various examples of the present disclosure may be generally suitable for use in any medical procedure that may use optical imaging systems.

Figure 2A:
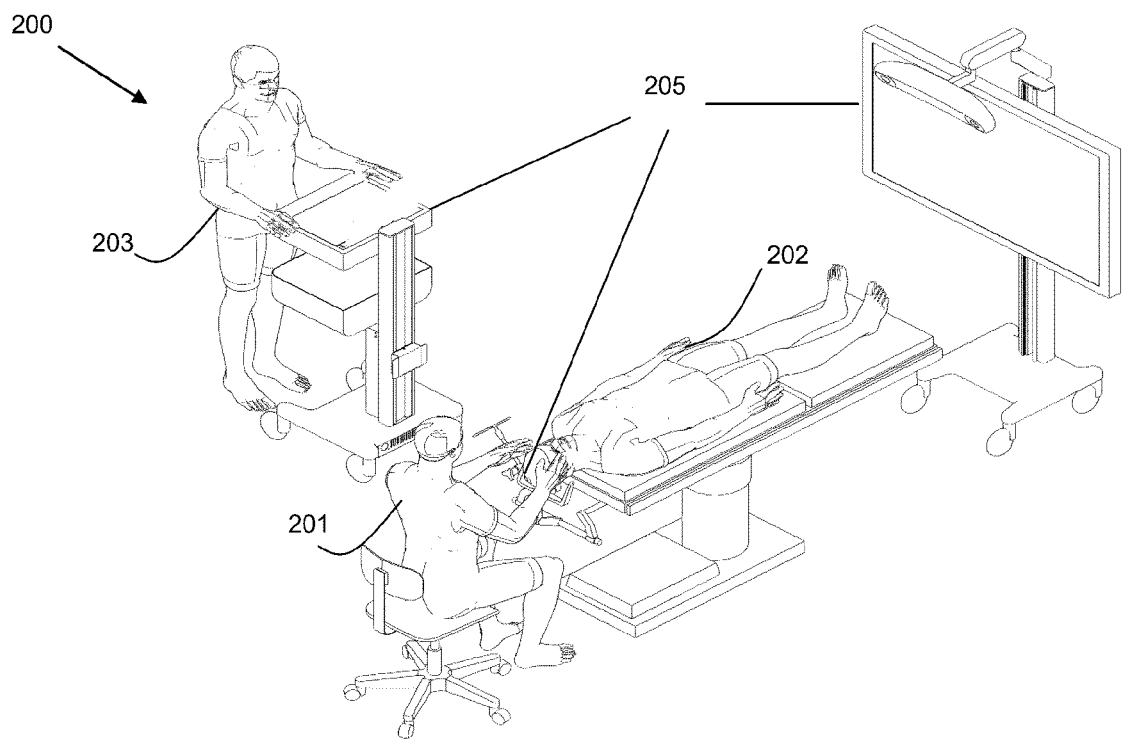
FIG. 2A shows an example navigation system to support image guided surgery.

In FIG. 2A, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 may include an equipment tower, tracking system, displays and tracked instruments to assist the surgeon 201 during his procedure. An operator 203 may also be present to operate, control and provide assistance for the medical navigation system 205.

Figure 2B:
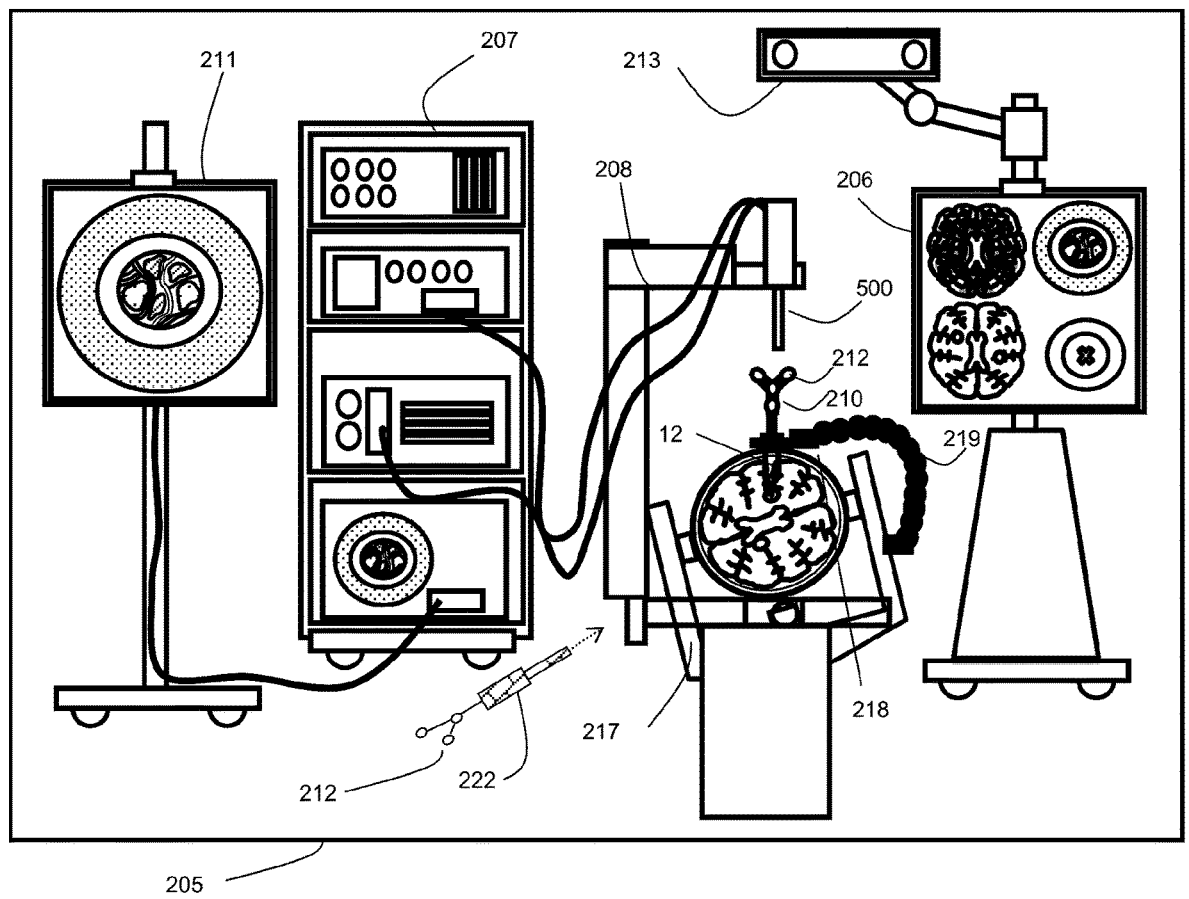
FIG. 2B is a diagram illustrating system components of an example navigation system.

FIG. 2B shows a diagram illustrating an example medical navigation system 205 in greater detail. The disclosed optical imaging system may be used in the context of the medical navigation system 205. The medical navigation system 205 may include one or more displays 206, 211 for displaying a video image, an equipment tower 207, and a positioning system 208, such as a mechanical arm, which may support an optical imaging system 500 (which may include an optical scope). One or more of the displays 206, 211 may include a touch-sensitive display for receiving touch input. The equipment tower 207 may be mounted on a frame (e.g., a rack or cart) and may contain a power supply and a computer or controller that may execute planning software, navigation software and/or other software to manage the positioning system 208 one or more instruments tracked by the navigation system 205. In some examples, the equipment tower 207 may be a single tower configuration operating with dual displays 206, 211, however other configurations may also exist (e.g., dual tower, single display, etc.). Furthermore, the equipment tower 207 may also be configured with a universal power supply (UPS) to provide for emergency power, in addition to a regular AC adapter power supply.

A portion of the patient's anatomy may be held in place by a holder. For example, as shown the patient's head and brain may be held in place by a head holder 217. An access port 12 and associated introducer 210 may be inserted into the head, to provide access to a surgical site in the head. The imaging system 500 may be used to view down the access port 12 at a sufficient magnification to allow for enhanced visibility down the access port 12. The output of the imaging system 500 may be received by one or more computers or controllers to generate a view that may be depicted on a visual display (e.g., one or more displays 206, 211).

In some examples, the navigation system 205 may include a tracked pointer 222. The tracked pointer 222, which may include markers 212 to enable tracking by a tracking camera 213, may be used to identify points (e.g., fiducial points) on a patient. An operator, typically a nurse or the surgeon 201, may use the tracked pointer 222 to identify the location of points on the patient 202, in order to register the location of selected points on the patient 202 in the navigation system 205. It should be noted that a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Fiducial markers 212 may be connected to the introducer 210 for tracking by the tracking camera 213, which may provide positional information of the introducer 210 from the navigation system 205. In some examples, the fiducial markers 212 may be alternatively or additionally attached to the access port 12. In some examples, the tracking camera 213 may be a 3D infrared optical tracking stereo camera similar to one made by Northern Digital Imaging (NDI). In some examples, the tracking camera 213 may be instead an electromagnetic system (not shown), such as a field transmitter that may use one or more receiver coils located on the tool(s) to be tracked. A known profile of the electromagnetic field and known position of receiver coil(s) relative to each other may be used to infer the location of the tracked tool(s) using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the positioning system 208 and/or access port 12 may be determined by the tracking camera 213 by detection of the fiducial markers 212 placed on or otherwise in fixed relation (e.g., in rigid connection) to any of the positioning system 208, the access port 12, the introducer 210, the tracked pointer 222 and/or other tracked instruments. The fiducial marker(s) 212 may be active or passive markers. A display 206, 2011 may provide an output of the computed data of the navigation system 205. In some examples, the output provided by the display 206, 211 may include axial, sagittal and coronal views of patient anatomy as part of a multi-view output.

The active or passive fiducial markers 212 may be placed on tools (e.g., the access port 12 and/or the imaging system 500) to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom (e.g., x, y, z coordinates and pitch, yaw, roll rotations), in five degrees of freedom (e.g., x, y, z, coordinate and two degrees of free rotation), but preferably tracked in at least three degrees of freedom (e.g., tracking the position of the tip of a tool in at least x, y, z coordinates). In typical use with navigation systems, at least three markers 212 are provided on a tracked tool to define the tool in virtual space, however it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the Polaris® system available from Northern Digital Inc. In some examples, the spatial position and orientation of the tracked tool and/or the actual and desired position and orientation of the positioning system 208 may be determined by optical detection using a camera. The optical detection may be done using an optical camera, rendering the markers 212 optically visible.

In some examples, the markers 212 (e.g., reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 205. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 205. The markers 212 may be tracked relative to a reference point or reference object in the operating room, such as the patient 202.

Various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

In some examples, the markers 212 may include printed or 3D designs that may be used for detection by an auxiliary camera, such as a wide-field camera (not shown) and/or the imaging system 500. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 212, the contours of known objects (e.g., the side of the access port 206) could be captured by and identified using optical imaging devices and the tracking system.

A guide clamp 218 (or more generally a guide) for holding the access port 12 may be provided. The guide clamp 218 may allow the access port 206 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

In a surgical operating room (or theatre), setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras to enable video overlay information. Video overlay information can then be inserted into displayed images, such as images displayed on one or more of the displays 206, 211. The overlay information may illustrate the physical space where accuracy of the 3D tracking system (which is typically part of the navigation system) is greater, may illustrate the available range of motion of the positioning system 208 and/or the imaging system 500, and/or may help to guide head and/or patient positioning.

The navigation system 205 may provide tools to the neurosurgeon that may help to provide more relevant information to the surgeon, and may assist in improving performance and accuracy of port-based neurosurgical operations. Although described in the present disclosure in the context of port-based neurosurgery (e.g., for removal of brain tumors and/or for treatment of intracranial hemorrhages (ICH)), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 may be used for carrying out any or all of these procedures, with or without modification as appropriate.

For example, although the present disclosure may discuss the navigation system 205 in the context of neurosurgery, the same navigation system 205 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the navigation system 205.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 3:
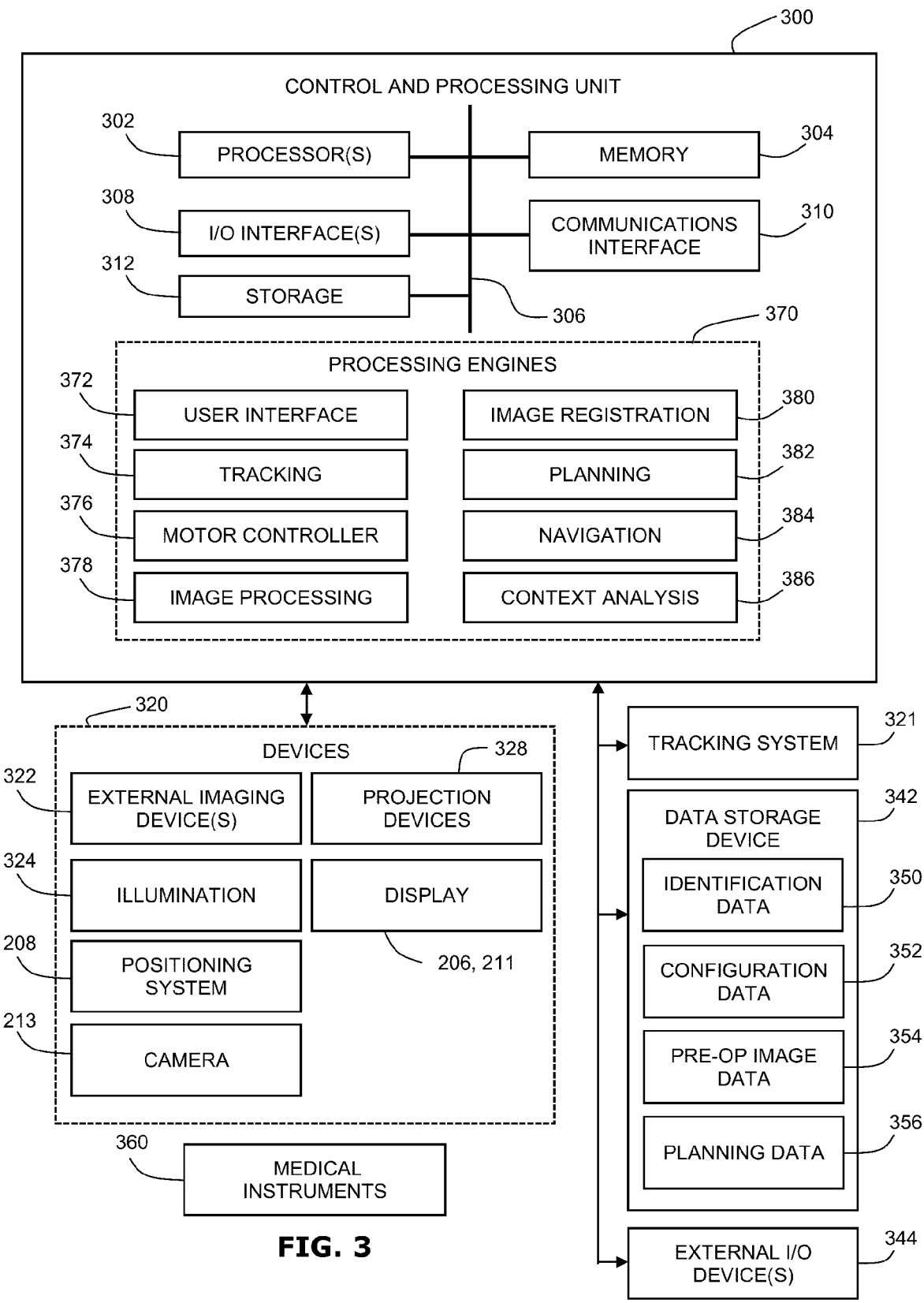
FIG. 3 is a block diagram illustrating an example control and processing system that may be used in the example navigation systems of FIGS. 2A and 2B.

FIG. 3 is a block diagram illustrating a control and processing system 300 that may be used in the medical navigation system 205 shown in FIG. 2B (e.g., as part of the equipment tower 207). As shown in FIG. 3, in one example, control and processing system 300 may include one or more processors 302, a memory 304, a system bus 306, one or more input/output interfaces 308, a communications interface 310, and storage device 312. The control and processing system 300 may be interfaced with other external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by the tracking camera 213. In one example, the tracking camera 213 may be an infrared (IR) tracking camera. In another example, as sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, the positioning system 208, the tracking camera 213, one or more projection devices 328, and one or more displays 206, 211.

Exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g., stored in the memory 304) rather than distinct sets of instructions.

It is to be understood that the system is not intended to be limited to the components shown in FIG. 3. One or more components of the control and processing system 300 may be provided as an external component or device. In one example, the navigation module 384 may be provided as an external navigation system that is integrated with the control and processing system 300.

Some embodiments may be implemented using the processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

In some examples, the navigation system 205, which may include the control and processing unit 300, may provide tools to the surgeon that may help to improve the performance of the medical procedure and/or post-operative outcomes. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be applied to any suitable medical procedure.

Figure 4A:
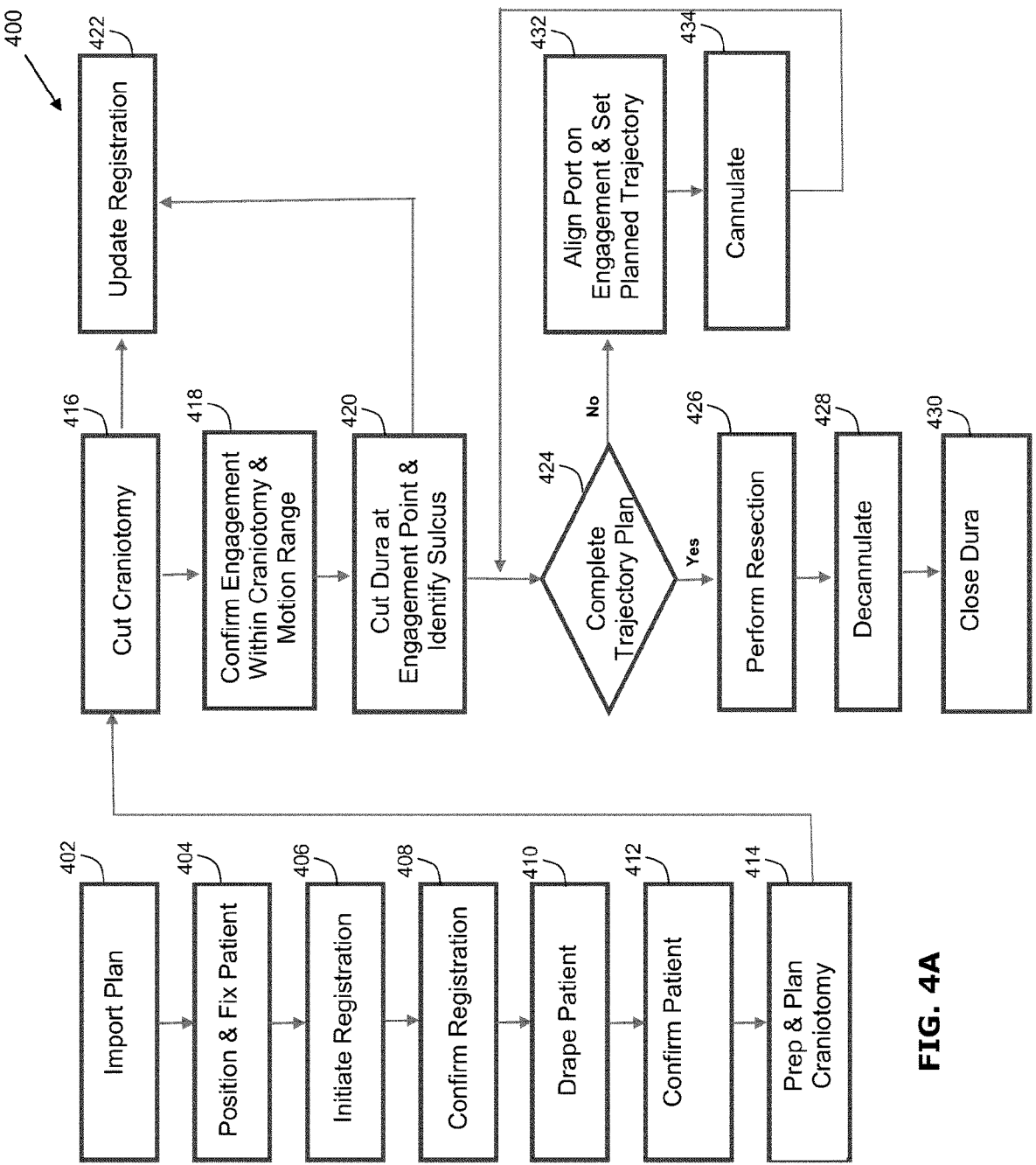
FIG. 4A is a flow chart illustrating an example method involved in a surgical procedure that may be implemented using the example navigation systems of FIGS. 2A and 2B.

FIG. 4A is a flow chart illustrating an example method 400 of performing a port-based surgical procedure using a navigation system, such as the medical navigation system 205 described in relation to FIGS. 2A and 2B. At a first block 402, the port-based surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower 207.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
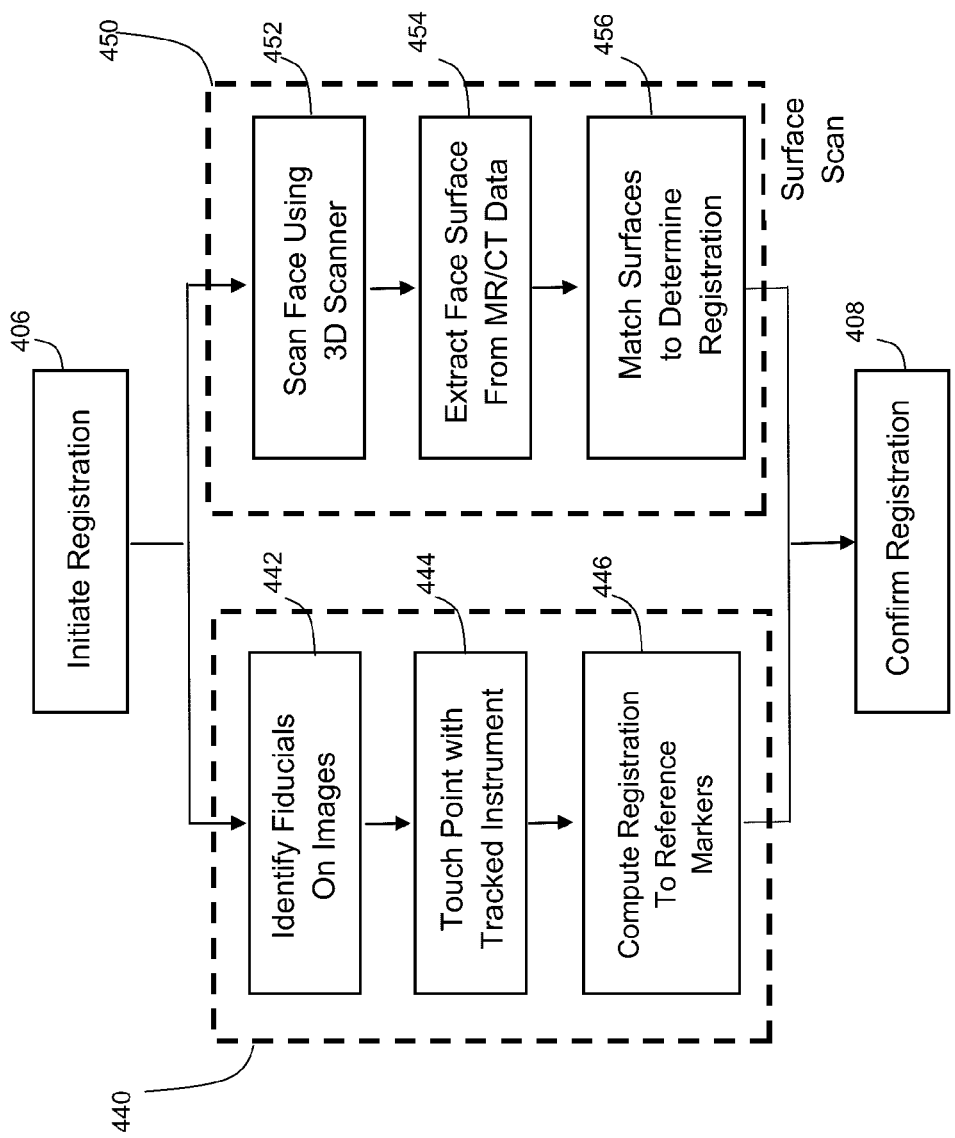
FIG. 4B is a flow chart illustrating an example method of registering a patient for a surgical procedure as outlined in FIG. 4A.

FIG. 4B is a flow chart illustrating an example method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 may acquire and maintain a reference of the location of the tools in use as well as the patient in three dimensional (3D) space. In other words, during a navigated neurosurgery, there may be a tracked reference frame that is fixed (e.g., relative to the patient's skull). During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
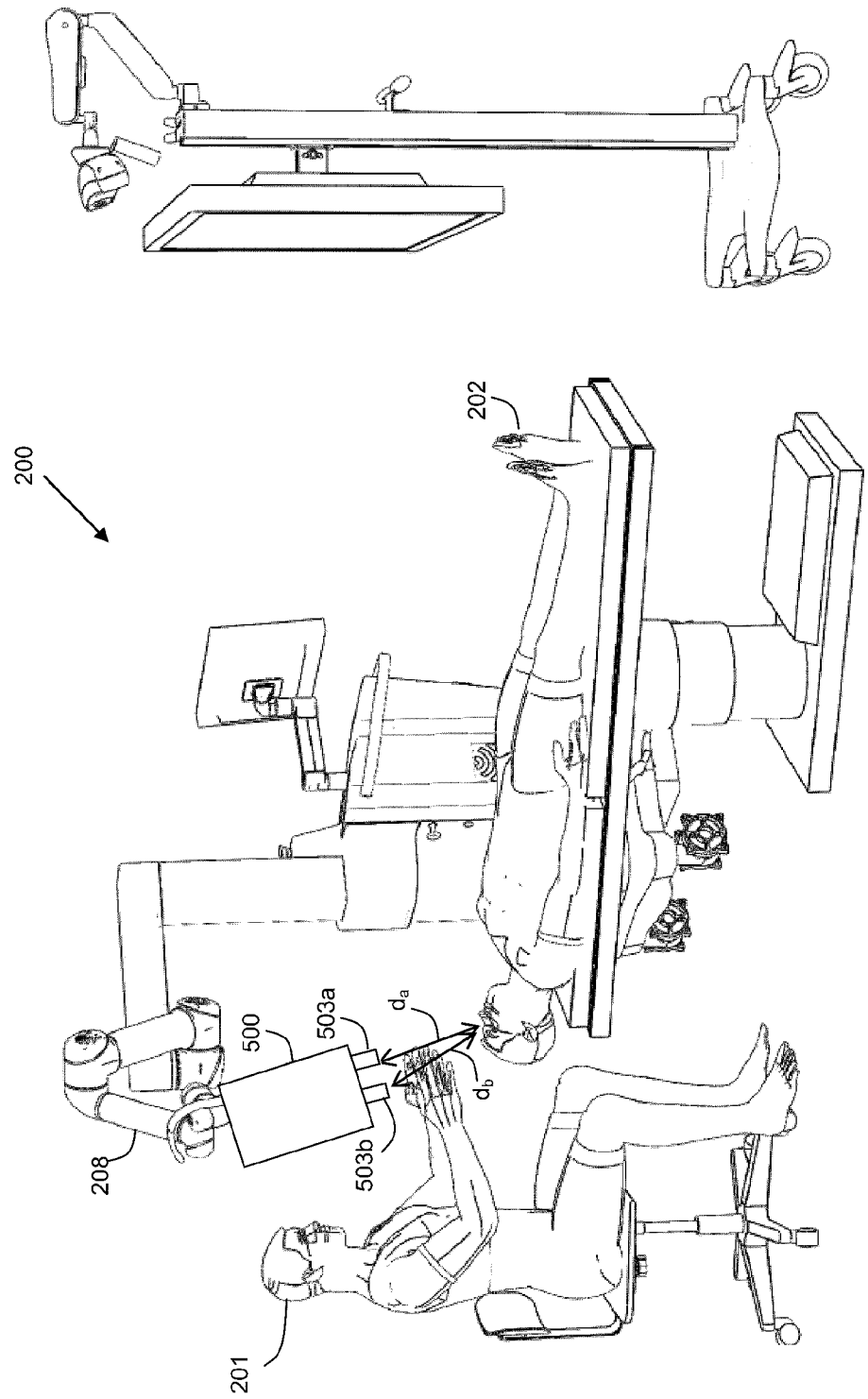
FIG. 5 shows the use of an example optical imaging system during a medical procedure.

FIG. 5 illustrates use of an example imaging system 500, described further below, in a medical procedure. Although FIG. 5 shows the imaging system 500 being used in the context of a navigation system environment 200 (e.g., using a navigation system as described above), the imaging system 500 may also be used outside of a navigation system environment (e.g., without any navigation support).

An operator, typically a surgeon 201, may use the imaging system 500 to observe the surgical site (e.g., to look down an access port). The imaging system 500 may be attached to a positioning system 208 (e.g., a controllable and adjustable robotic arm). The position and orientation of the positioning system 208, imaging system 500 and/or access port may be tracked using a tracking system, such as described for the navigation system 205. As described below, the imaging system 500 may include two apertures 503a, 503b, one for each optical assembly. The apertures 503a, 503b of each optical assembly may be independently adjustable, which may enable each optical assembly to have independently controllable resolution and depth-of-field. The distances $d_a$, $d_b$ between each aperture 503a, 503b of the imaging system 500 and the viewing target (e.g., the surface of the surgical site) may be referred to as the respective working distance of each optical assembly. The imaging system 500 may be designed to be used in a predefined range of working distance (e.g., in the range of about 20 cm to about 65 cm). It should be noted that, if the imaging system 500 is mounted on the positioning system 208, the actual available range of working distance may be dependent on both the working distance of the imaging system 500 as well as the workspace and kinematics of the positioning system 208.

Figure 6:
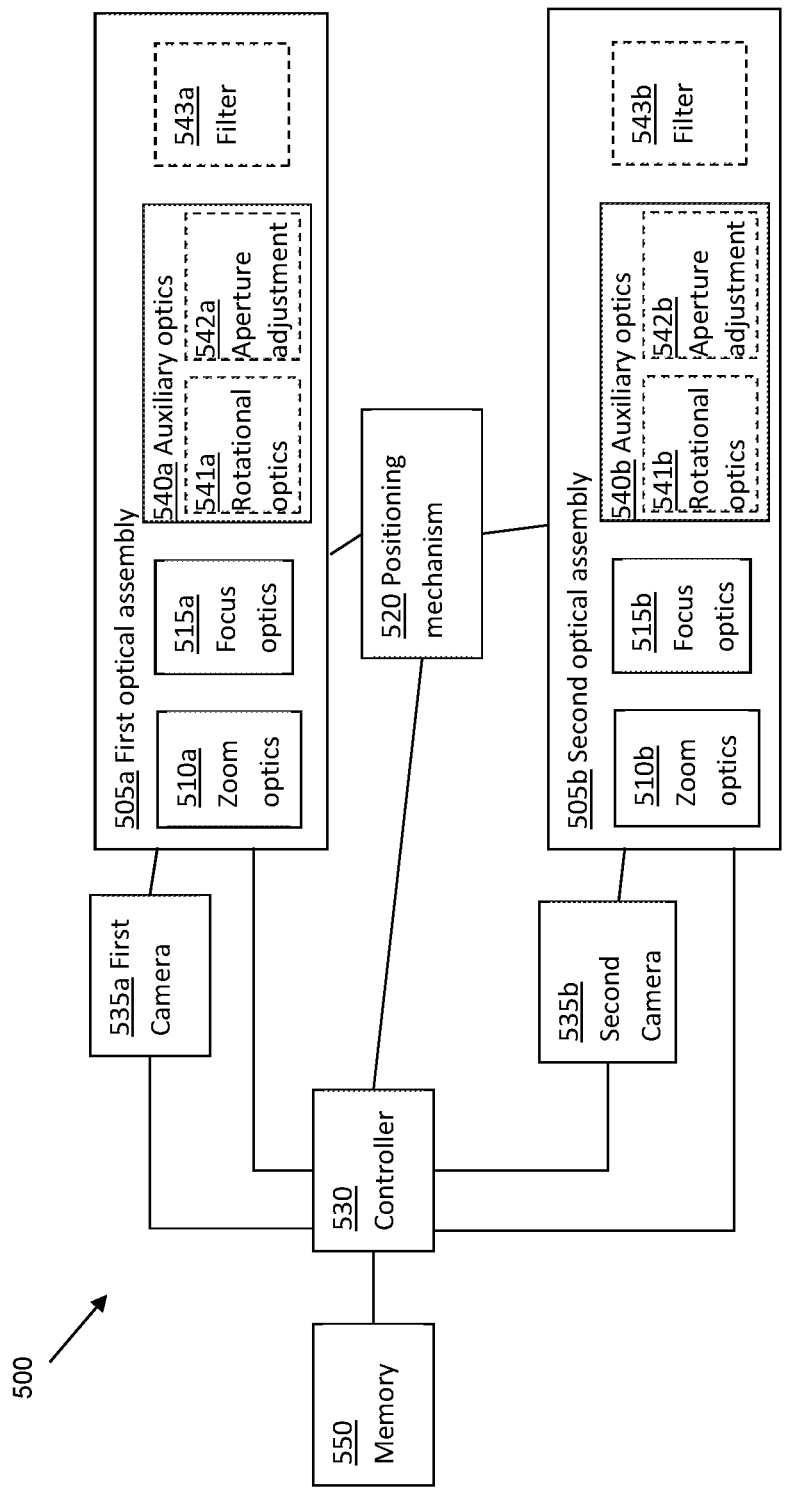
FIG. 6 is a block diagram of an example optical imaging system.

FIG. 6 is a block diagram showing components of an example imaging system 500. The imaging system 500 includes first and second optical assemblies 505a, 505b (also referred to as optical trains), each of which may be operated independently or cooperatively. Each optical assembly 505a, 505b may capture an image received through respective apertures 503a, 503b (see FIG. 6).

For simplicity, the first optical assembly 505a will be described in detail; the second optical assembly 505b may have the same components and function as the first optical assembly 505a, for example as described below. The first optical assembly 505a comprises optics (e.g., lenses, optical fibers, etc.) for focusing and zooming on the viewing target. The first optical assembly 505a comprises zoom optics 510a (which may comprise one or more zoom lenses) and focus optics 515a (which may include one or more focus lenses). Each of the zoom optics 510a and focus optics 515a are independently moveable within the first optical assembly 505a, in order to adjust the zoom and focus, respectively. Where the zoom optics 510a and/or the focus optics 515a comprise more than one lens, each individual lens is independently moveable. The aperture 503a of the first optical assembly 505a may be adjustable. The first optical assembly 505a comprises one or more auxiliary optics 540a (e.g., rotational optics 541a and/or aperture adjustment 542a), which may be static or dynamic. For example, the auxiliary optics 540a comprise rotational optics 541a (e.g., prisms) to enable the user to define the orientation of the captured image. The rotational optics 541a of the first optical assembly 505a are independently adjustable, thereby enabling the first optical assembly 505a to independently capture rotation images in relation to the second optical assembly 505b. Alternatively, instead of using rotation optics 541a, software image processing may be performed to rotate a captured image to the desired orientation. The first optical assembly 505a comprises one or more filters 543a, each filter 543a being independently configurable (e.g., for different wavelengths, polarizations, neutral densities, or other characteristics) in relation to any other filter 543a. The filters 543a are disposable in the optical path (e.g., using filter wheels or other similar mechanism). The first optical assembly 505a comprises a plurality of different filters 543a. The second optical assembly 505b comprises optics (e.g., lenses, optical fibers, etc.) for focusing and zooming on the viewing target. The second optical assembly 505b comprises zoom optics 510b (which may include one or more zoom lenses) and focus optics 515b (which may include one or more focus lenses). Each of the zoom optics 510b and focus optics 515b are independently moveable within the second optical assembly 505b, in order to adjust the zoom and focus, respectively. Where the zoom optics 510b and/or the focus optics 515b comprise more than one lens, each individual lens is independently moveable. The aperture 503b of the second optical assembly 505b is adjustable. The second optical assembly 505b further comprises one or more auxiliary optics 540b (e.g., rotational optics 541b and/or aperture adjustment 542b), which may be static or dynamic. For example, the auxiliary optics 540b comprise rotational optics 541b (e.g., prisms) to enable the user to define the orientation of the captured image. The rotational optics 541b of the second optical assembly 505b are independently adjustable, thereby enabling the second optical assembly 505b to independently capture rotation images in relation to the first optical assembly 505a. Alternatively, instead of using rotation optics 541b, software image processing may be performed to rotate a captured image to the desired orientation. The second optical assembly 505b comprises one or more filters 543b, each filter 543b being independently configurable (e.g., for different wavelengths, polarizations, neutral densities, or other characteristics) in relation to any other filter 543b. The filters 543b are disposable in the optical path (e.g., using filter wheels or other similar mechanism). The second optical assembly 505b comprises a plurality of different filters 543b.

The imaging system 500 may include one or more positioning mechanisms 520 (e.g., gear train, rack and gear system, conveyor mechanism or linear stage mechanism) for positioning the first and second optical assemblies 505a, 505b relative to each other. For simplicity, the present disclosure may refer to the positioning mechanism 520 in the singular, however the present disclosure also includes embodiments where the positioning mechanism 520 includes a plurality of such mechanisms.

In some examples, the imaging system 500 may include a light source or may direct light from an external light source, for illuminating the viewing target. The light source (whether internal or external to the imaging system 500) may be capable of providing different wavelengths of light and different bandwidths, for example including broadband illumination for white light imaging, or narrow band illumination in the fluorescence spectrum for fluorescence imaging. Fluorescence imaging typically involves the use of appropriate excitation and emission filters. The wavelength characteristics of the filter are typically specific to the fluorophore used.

Figure 7:
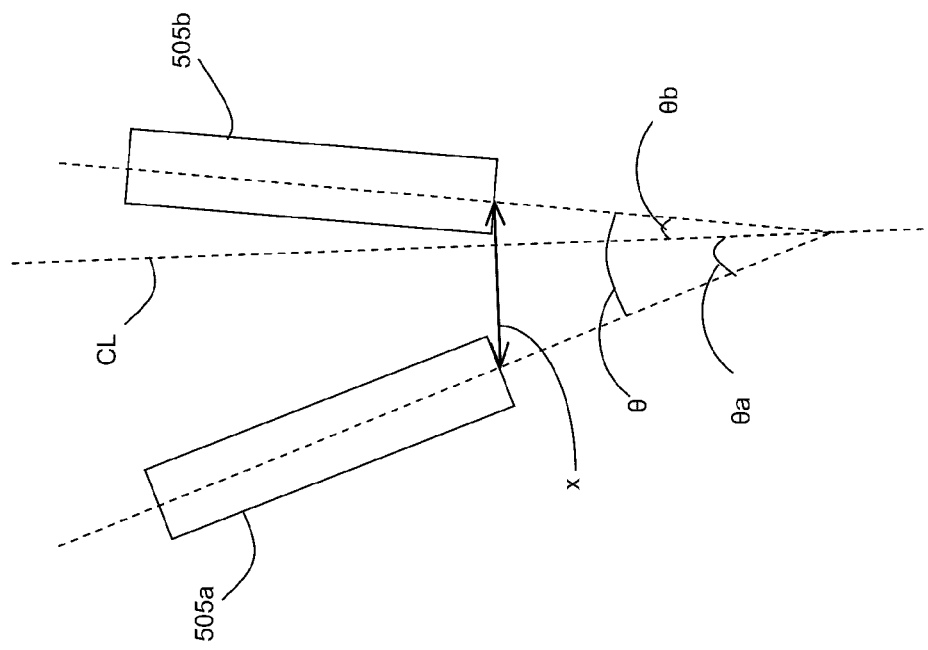
FIG. 7 is a block diagram illustrating relative position and orientation of optical assemblies an example optical imaging system.

Throughout the present disclosure, the positions and orientations of the optical assemblies 505a, 505b may be described with reference to the optical axes of each optical assembly 505a, 505b. Generally, the optical axis of an optical assembly 505a, 505b may be defined as the axis along which light travels from the viewing target to the aperture of the optical assembly 505a, 505b, and is typically the longitudinal axis of the optical assembly 505a, 505b. It should be noted that the working distance of the optical assembly 505a, 505b is typically also measured along the optical axis. The positioning mechanism 520 may be used to control the lateral separation x between the optical axes of the optical assemblies 505a, 505b, and the angle θ between the optical axes of the optical assemblies 505a, 505b (see FIG. 7). Where the optical axes are not parallel to each other, lateral separation between the optical axes may be measured as the lateral distance between the apertures of the optical assemblies 505a, 505b. The angle θ between the optical axes may be alternatively defined as the summation of respective angles θa, θb of each optical axis relative to a common centerline CL of the imaging system 500. In some examples, the positioning mechanism 520 may include separate mechanisms for controlling position and orientation of each optical assembly 505a, 505b. In some examples, the same positioning mechanism 520 may be used to control position and orientation of both optical assemblies 505a, 505b. The lateral separation and angle may be separately and independently controlled, and may be controlled using separate positioning mechanisms 520 for lateral separation and for angular orientation.

Operation of the optics in the first and second optical assemblies 505a, 505b may be controlled by a controller 530 (e.g., a microprocessor) of the imaging system 500. The controller 530 may receive control input (e.g., from an external system, such as an external processor or an input device). The control input may direct the controller 530 to control the optical assemblies 505a, 505b in one of various possible modes of operation, as discussed further below. The controller 530 may directly control movement of the zoom optics 510a, 510b and/or the focus optics 515a, 515b, or the controller 530 may provide instructions to a respective sub-controller (not shown) of each optical assembly 505a, 505b to control the respective zoom optics 510a, 510b and/or focus optics 515a, 515b.

The controller 530 may also control the positioning mechanism 520 to control the relative position and orientation of the optical assemblies 505a, 505b. For example, the controller 530 may control the positioning mechanism 520 to position/orient only one of the optical assemblies 505a, 505b, each optical assembly 505a, 505b independently of the other, both optical assemblies 505a, 505b simultaneously and/or both optical assemblies 505a, 505b cooperatively, as discussed further below.

The imaging system 500 may also include first and second cameras 535a, 535b (e.g., high-definition (HD) cameras) for each respective optical assembly 505a, 505b to capture image data from the respective optical assembly 505a, 505b. Operation of the cameras 535a, 535b may be controlled by the controller 530. The cameras 535a, 535b may also output data to an external system (e.g., an external workstation or external output device) to view the captured image data. In some examples, the cameras 535a, 535b may output data to the controller 530, which in turn transmits the data to an external system for viewing. By providing image data to an external system for viewing, the captured images may be viewed on a larger display and may be displayed together with other information relevant to the medical procedure (e.g., a wide-field view of the surgical site, navigation markers, 3D images, etc.).

The controller 530 may be coupled to a memory 550. The memory 550 may be internal or external of the imaging system 500. Data received by the controller 530 (e.g., image data from the cameras 535a, 535b) may be stored in the memory 550. The memory 550 may also contain instructions to enable the controller to operate the positioning mechanism 520 and/or to control the zoom and focus of each optical assembly 505a, 505b. For example, the memory 550 may store instructions to enable the controller to control the optical assemblies 505a, 505b independently or cooperatively, as discussed further below.

The imaging system 500 may communicate with an external system (e.g., a navigation system or a workstation) via wired or wireless communication. In some examples, the imaging system 500 may include a wireless transceiver (not shown) to enable wireless communication. An external processor (e.g., a processor of a workstation or the navigation system) in communication with the controller 530 may be used to provide control input to the controller 530. For example, the external processor may provide a graphical user interface via which the operator or an assistant may input instructions to control operation of the imaging system 500. The controller 530 may alternatively or additionally be in communication with an external input system (e.g., a voice recognition input system or a foot pedal).

In some examples, the imaging system 500 may include a power source (e.g., a battery) or a connector to a power source (e.g., an AC adaptor). In some examples, the imaging system 500 may receive power via a connection to an external system (e.g., an external workstation or processor).

In some examples, the first and second optical assemblies 505a, 505b may be housed in a common housing (not shown). The housing may be sized to allow relative movement between the optical assemblies 505a, 505b, within preset boundaries. In some examples, other components of the imaging system 500 may also be housed in the same housing.

The imaging system 500 may be mountable on a moveable support structure, such as the positioning system (e.g., robotic arm) of a navigation system, a manually operated support arm, a ceiling mounted support, a moveable frame, or other such support structure. The imaging system 500 may be removably mounted on the moveable support structure. In some examples, the imaging system 500 may include a support connector (e.g., a mechanical coupling) to enable the imaging system 500 to be quickly and easily mounted or dismounted from the support structure. The support connector on the imaging system 500 may be configured to be suitable for connecting with a typical complementary connector on the support structure (e.g., as designed for typical end effectors). In some examples, the imaging system 500 may be mounted to the support structure together with other end effectors, or may be mounted to the support structure via another end effector.

When mounted, the imaging system 500 may be at a known fixed position and orientation relative to the support structure (e.g., by calibrating the position and orientation of the imaging system 500 after mounting). In this way, by determining the position and orientation of the support structure (e.g., using a navigation system or by tracking the movement of the support structure from a known starting point), the position and orientation of the imaging system 500 may also be determined. In some examples, the imaging system 500 may include a manual release button that, when actuated, enable the imaging system 500 to be manually positioned (e.g., without software control by the support structure).

As discussed above, the two optical assemblies of the imaging system may be controlled independently or cooperatively. The magnification and focus of each optical assembly may similarly be controlled independently or cooperatively between the optical assemblies. The imaging system may operate in one of several modes: for example including independent mode, dual-FOV mode, stereoscopic mode, and depth map mode. The imaging system may receive control input from an external system or from a input mechanism to select the mode of operation and to switch between different modes of operation. The surgeon or other operator may control the imaging system to switch between different modes of operation intraoperatively.

In the independent mode, the controller may control each optical assembly independently, such that the two optical assemblies may function similarly to two separate microscopes and may capture images of different target objects. The controller may control the zoom and focus optics of each optical assembly independently, in response to control input. Each optical assembly may also be positioned and oriented independently of each other (within the constraint that the optical assemblies should not collide with each other), in order to capture different FOVs, for example. The cameras associated with each optical assembly may also operate independently. Image data from each optical assembly may be communicated separately and may be displayed separately. For example, the first optical assembly and first camera may capture images of a first target, and this image data may be communicated to a desktop computer for display on a desktop display; the second optical assembly and second camera may capture images of a second target, and this image data may be communicated to a projection device for display on a projection screen. In some examples, the captured images may be displayed side-by-side on the same display device. The controller of the imaging system may manage and route the image data accordingly, in response to the operator's control input.

In the dual-FOV mode, the optical assemblies may be controlled to view the same target object. However, the zoom optics of each optical assembly may be controlled separately such that the first optical assembly provides a FOV that is different from the FOV of the second optical assembly. Each optical assembly may thus provide a respective two-dimensional (2D) view of the target object, but with different FOVs. For example, the first optical assembly may provide a larger FOV than the second optical assembly, and the FOV provided by the second optical assembly may fall entirely within the FOV of the first optical assembly. The FOV of each optical assembly may be controlled independently, in response to control input. The surgeon may control the imaging system to focus on a certain target object and may select the zoom or FOV size for each optical assembly. As the imaging system is controlled to view different viewing targets, each optical assembly may change its focus accordingly, while maintaining the respective selected zoom. In some examples, the zoom or FOV size for each optical assembly may be selected by specifying a relative difference between the zooms or FOV sizes (e.g., presetting that one FOV should be twice the magnification of the other FOV); and/or may be selected by specifying the zoom or FOV size explicitly (e.g., in percentage magnification). Since the FOV of each optical assembly may be controlled independently, one FOV may be fixed while the other is varied, the two FOVs may be the same, and the optical assemblies may switch between having larger or smaller FOVs between the two, for example. The use of the dual-FOV mode may provide the surgeon with a magnified view of the surgical target while simultaneously providing the surgeon with a wider contextual view of the surgical field. Similarly to the independent mode, the image data captured by the first and second cameras may be displayed separately or side-by-side, for example.

In some examples, 3D images may be obtained using the dual-FOV mode. For example, where the FOV of the first optical assembly overlaps with or entirely includes the FOV of the second optical assembly, both sets of image data may be communicated to an external system (e.g., an image viewing workstation). The external system may determine the image portion that is common between the two FOVs and may generate a 3D image (e.g., using appropriate 3D image rendering techniques), using the two sets of image data, for this common image portion.

In the stereoscopic mode, the optical assemblies may be controlled to view the same target object using the same FOV. Because of the separation of the optical assemblies, the result is that the two optical assemblies may cooperate together to function similarly to a stereoscopic microscope, with the cameras of each optical assembly being used to capture a respective one of a pair of stereo images. The surgeon may control the imaging system to focus on a certain target object at a certain FOV. As the imaging system is controlled to view different viewing targets, each optical assembly may change its focus accordingly so that they continue to focus on a common viewing target. The surgeon may control the imaging system to change the zoom or FOV, and each optical assembly may adjust its zoom accordingly. The image data captured by the first and second cameras may be communicated to an external system (e.g., an image viewing workstation) that may use the two sets of data to generate a 3D image (e.g., using appropriate 3D rendering techniques). The 3D image may be presented as a rendered 3D model on a conventional 2D display, and/or may be viewed as a 3D image using 3D viewing technology (e.g., requiring the use of 3D glasses). The 3D image may be provided as part of an augmented reality display, for example. In some examples, the imaging system in the stereoscopic mode may operate similarly to the dual-FOV mode, with the difference that the two optical assemblies share the same FOV.

In some examples, the image data captured using the disclosed imaging system may be used for an augmented reality display. Using augmented reality, video information captured by the imaging system may be displayed together with images from other imaging modalities (e.g., intra-operative imaging modalities such as optical coherence tomography (OCT), ultrasound, fluorescence imaging and elastography, or pre-operative imaging modalities such as MRI, CT, PET, functional MRI (fMRI) and diffusion tensor imaging (DTI)). The image information captured from both optical assemblies may be at the same level of magnification to provide a 3D stereoscopic view of the target (e.g., as described above), or at different levels of magnification to provide different FOVs, for example. When different FOVs are provided, using augmented reality to superimpose anatomical structures on the narrower FOV may help the surgeon to reduce or avoid the risk of damaging brain cells while a wider FOV overlay may provide information to help enhance the surgeon's understanding of the spatial relationship between different structures and their functional status.

It should be noted that, unlike conventional stereoscopic microscopes, the disclosed imaging system allows for the lateral separation of the optical assemblies to be adjusted. Since there is a relationship between lateral stereo separation and working distance, the ability of the disclosed imaging system to dynamically adjust lateral separation may provide for a more comfortable viewing experience (e.g., enabling more comfortable viewing of 3D images, with less eye strain and/or headaches), for example by more accurately mimicking the natural separation between the viewer's eyes.

In the depth map mode, each optical assembly may be used to view a different depth of field, while focused on the same target object and in the same FOV. For example, the first optical assembly may provide a greater depth of field (e.g., 1 cm) than the second optical assembly (e.g., 1 mm). The second optical assembly may be controlled to automatically move through the depth range of the first optical assembly to capture images at different depths (e.g., at increments of 1 mm) through the depth range. The image data captured by the second optical assembly at different depths may be transmitted, together with the image data captured by the first optical assembly, to an external system (e.g., an image viewing workstation). The image data from the second optical assembly at different depths may be aggregated into a set of depth images to form a depth map for the same FOV as the image data from the first optical assembly. The depth map may provide focused views of the FOV, at different depths, and may include contours, color-coding and/or other indicators of different depths. Image processing may be performed to generate a pseudo 3D image, for example by visually encoding (e.g., using color, artificial blurring or other visual symbols) different parts of the captured image according to the depth information. The external system may provide a user interface that allows a user to navigate through the depth map, for example.

In some examples, a depth map may be generated by comparing image information from two different vantage points coming from the two optical assemblies. The apparent pixel difference between these two images, also referred to as a disparity map, may be used to generate a depth map.

Examples of the present disclosure may enable different viewing modes (e.g., stereoscopic mode and dual-FOV mode) to be implemented using a single imaging system, without having to switch between different imaging systems. An operator may conveniently switch between the different modes depending on the desired imaging.

Although the above examples describe the use of an external system such as an image viewing workstation for processing image data from the imaging system, in some examples some or all of the image processing may be performed by the controller of the imaging system itself.

Generally, when operating in the independent mode, the controller of the imaging system may control the optical assemblies in an uncoupled configuration, where each optical assembly is controlled entirely independently of the other. When in the uncoupled configuration, the positioning mechanism may mechanically uncouple the optical assemblies from each other. In some examples where there are separate positioning mechanisms for each optical assembly, the positioning mechanisms may simply operate independently.

When operating in the dual-FOV mode, the stereoscopic mode or the depth map mode, the controller may control the optical assemblies in a coupled configuration, where the focus and/or zoom of one optical assembly is dependent on that of the other, and where the position and/or orientation of one optical assembly is dependent on that of the other. For example, the optical axes and/or focus optics of each optical assembly may be adjusted so that a common focus is maintained even as the viewing target is moved, or as the working distance is adjusted. When in the coupled configuration, the positioning mechanism may serve to mechanically couple the optical assemblies to each other.

In some examples, the disclosed imaging system may be used with a navigation system (e.g., as described above). The navigation system may provide tracking of a viewing target (e.g., by tracking a pointer tool or other medical instrument) and the controller may control the imaging system to automatically adjust focus to follow the tracked target. The navigation system may also provide information to help with positioning of the imaging system relative to the tracked target (e.g., using a robotic positioning system).

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A surgical imaging system configured to communicate with a navigation system and to couple with a positioning system of the navigation system, the imaging system comprising:
    a first optical assembly defining a first optical axis and comprising a first set of optics for adjusting a first field-of-view (FOV) and a first focus, a first aperture for receiving light from the first FOV, a first set of auxiliary optics comprising a first set of rotational optics, and a first camera for capturing a first image of the first FOV;
    a second optical assembly defining a second optical axis and comprising a second set of optics for adjusting a second FOV and a second focus, a second aperture for receiving light from the second FOV, a second set of auxiliary optics comprising a second set of rotational optics, and a second camera for capturing a second image of the second FOV; and
    a controller operable with an external system and configured to execute a set of computer-executable instructions for: controlling mechanical positioning of the first and the second optical assemblies, switching the surgical imaging system between a coupled configuration and an uncoupled configuration, and switching the surgical imaging system between a first viewing mode and a second viewing mode during surgery, and the instructions configuring the controller to:
    when the surgical imaging system is in the coupled configuration, control the first and the second optical assemblies to adjust at least one of: the respective first and second sets of optics; and the respective first and second optical axes in dependence on each other; and
    when the surgical imaging system is in the uncoupled configuration, control the first and the second optical assemblies to adjust at least one of: the respective first and second sets of optics; and the respective first and second optical axes independently of each other,
    wherein the second FOV is distinct in relation to the first FOV, the second FOV corresponds to the second viewing mode distinct in relation to the first viewing mode of the first FOV, the second aperture is independently adjustable in relation to the first aperture, and the second set of rotational optics is independently adjustable in relation to the first set of rotational optics, and whereby the second optical assembly independently captures rotation images in relation to those of the first optical assembly,
    wherein at least one of the first optical assembly and the second optical assembly further comprises at least one optical filter, the at least one optical filter independently configured for a plurality of different wavelengths, a plurality of different polarizations, and a plurality of different neutral densities, and the at least one optical filter deployed in an optical path by a filter wheel, and
    wherein the at least one optical filter of the first optical assembly is distinct in relation to the at least one optical filter of the second optical assembly.

2. The surgical imaging system of claim 1, wherein the controller is further configured to control lateral separation of the first and second optical assemblies.

3. The surgical imaging system of claim 1, further comprising a positioning mechanism between the first and second optical assemblies, wherein the controller is further configured to control the first and second optical axes via the positioning mechanism.

4. The surgical imaging system of claim 1, wherein, in the uncoupled configuration, the controller is further configured to adjust the first and second optical assemblies independently to focus on different targets.

5. The surgical imaging system of claim 1, wherein, in the coupled configuration, the controller is further configured to adjust the first and second optical axes and the first and second sets of optics to focus on a common target and to produce different first and second FOVs.

6. The surgical imaging system of claim 1, wherein, in the coupled configuration, the controller is further configured to adjust the first and second optical axes and the first and second sets of optics to focus on a common target with a common FOV.

7. The surgical imaging system of claim 6, wherein the controller is further configured to control the first and second cameras to each capture a respective one of a pair of stereo images.

8. The surgical imaging system of claim 1, further comprising a light source for illuminating at least one FOV.

9. The surgical imaging system of claim 8, wherein the light source is capable of providing different wavelengths of light and different bandwidths for supporting broadband illumination, white light imaging, narrow band illumination, and fluorescence imaging.

10. The surgical imaging system of claim 1, wherein each aperture is independently adjustable in relation to the other aperture when the surgical imaging system is in the uncoupled configuration.

11. The surgical imaging system of claim 1, wherein each set of rotational optics is independently adjustable when the surgical imaging system is in the uncoupled configuration.

12. The surgical imaging system of claim 1, wherein the external system comprises a voice-recognition input system.

13. A processor for controlling a surgical imaging system configured to communicate with a navigation system and to couple with a positioning system of the navigation system, the surgical imaging system comprising:
   a first optical assembly defining a first optical axis, the first optical assembly comprising a first set of one or more optics for adjusting a first field-of-view (FOV) and a first focus, a first aperture for receiving light from the first FOV, a first set of auxiliary optics comprising a first set of rotational optics, and a first camera for capturing a first image of the first FOV;
   a second optical assembly defining a second optical axis, the second optical assembly comprising a second set of one or more optics for adjusting a second FOV and a second focus, a second aperture for receiving light from the second FOV, a second set of auxiliary optics comprising a second set of rotational optics, and a second camera for capturing a second image of the second FOV; and
   a controller operable with an external system and configured to execute a set of computer-executable instructions for: controlling mechanical positioning of the first and the second optical assemblies, switching the surgical imaging system between a coupled configuration and an uncoupled configuration, and switching the surgical imaging system between a first viewing mode and a second viewing mode during surgery, and the instructions configuring the controller to:
   when the surgical imaging system is in the coupled configuration, control the first and the second optical assemblies to adjust at least one of: the respective first and second sets of optics; and the respective first and second optical axes in dependence on each other; and
   when the surgical imaging system is in the uncoupled configuration, control the first and the second optical assemblies to adjust at least one of: the respective first and second sets of optics; and the respective first and second optical axes independently of each other,
   operate with the at least one external system,
   wherein the second FOV is distinct in relation to the first FOV, the second FOV corresponds to the second viewing mode in relation to the first viewing mode of the first FOV, the second aperture is independently adjustable in relation to the first aperture, and the second set of rotational optics is independently adjustable in relation to the first set of rotational optics, and whereby the second optical assembly independently captures rotation images in relation to those of the first optical assembly, and
   the processor is configured to: provide a user interface to receive control input, via an input device coupled to the processor, for controlling the optical imaging system; transmit control instructions to the controller of the optical imaging system to adjust at least one of: the respective first and second sets of optics; and the respective first and second optical axes in accordance with the control input; and receive image data from the first and second cameras for outputting to an output device coupled to the processor, and
   wherein at least one of the first optical assembly and the second optical assembly further comprises at least one optical filter, the at least one optical filter independently configured for a plurality of different wavelengths, a plurality of different polarizations, and a plurality of different neutral densities, and the at least one optical filter deployed in an optical path by a filter wheel, and
   wherein the at least one optical filter of the first optical assembly is distinct in relation to the at least one optical filter of the second optical assembly.

14. The processor of claim 13,
   wherein the user interface enables user selection of a mode of operation of the surgical imaging system, and
   wherein the control instructions cause the controller of the optical imaging system to configure the optical imaging system in one of the coupled configuration and the uncoupled configuration in dependence on a mode of operation.

15. The processor of claim 14, wherein the mode of operation is selected from a plurality of modes comprising an independent mode, a dual-FOV mode, a stereoscopic mode, and a depth-map mode.

16. The processor of claim 13, wherein the processor is further configured to receive a respective one of a pair of stereo images from the first and second cameras, respectively, and to generate a three-dimensional (3D) image from the pair of stereo images.

17. The processor of claim 13,
   wherein the processor is further configured to receive a first image, having a first FOV, from the first camera, and a second image, having a different second FOV, from the second camera,
   wherein the first FOV and the second FOV share an overlapping portion, and
   wherein the processor is further configured to generate a three-dimensional (3D) image from the overlapping portion.

18. The processor of claim 13, wherein the output device comprises an augmented reality display.

19. The processor of claim 18, wherein the processor is further configured to enable image data captured by the surgical imaging system to be displayed together with image data from at least one other imaging modality.

20. The processor of claim 19, wherein the at least one other imaging modality is selected from a list comprising: optical coherence tomography (OCT), ultrasound, fluorescence imaging, elastography, magnetic resonance imaging (MRI), computer tomography (CT), positron emission tomography (PET), functional MRI (fMRI), and diffusion tensor imaging (DTI).

21. A system for imaging a surgical site during a surgical procedure and configured to communicate with a navigation system and to couple with a positioning system of the navigation system, the imaging system comprising:
   a surgical imaging system comprising:
      a first optical assembly defining a first optical axis, the first optical assembly comprising a first set of one or more optics for adjusting a first field-of-view (FOV) and a first focus, a first aperture for receiving light from the first FOV, a first set of auxiliary optics comprising a first set of rotational optics, and a first camera for capturing a first image of the first FOV;
      a second optical assembly defining a second optical axis, the second optical assembly comprising a second set of one or more optics for adjusting a second FOV and a second focus, a second aperture for receiving light from the second FOV, a second set of auxiliary optics comprising a second set of rotational optics, and a second camera for capturing a second image of the second FOV; and
   a controller operable with an external system and configured to execute a set of computer-executable instructions for: controlling mechanical positioning of the first and the second optical assemblies, switching the surgical imaging system between a coupled configuration and an uncoupled configuration, and switching the surgical imaging system between a first viewing mode and a second viewing mode during surgery, and the instructions configuring the controller to:
   when the surgical imaging system is in the coupled configuration, control the first and the second optical assemblies to adjust at least one of: the respective first and second sets of optics; and the respective first and second optical axes in dependence on each other;
   when the surgical imaging system is in the uncoupled configuration, control the first and the second optical assemblies to adjust at least one of: the respective first and second sets of optics; and the respective first and second optical axes independently of each other; and
   operate with the at least one external system,
   wherein the second FOV is distinct in relation to the first FOV, the second FOV corresponds to the second viewing mode in relation to the first viewing mode of the first FOV, the second aperture is independently adjustable in relation to the first aperture, and the second set of rotational optics is independently adjustable in relation to the first set of rotational optics, and whereby the second optical assembly independently captures rotation images in relation to those of the first optical assembly;
   a display for displaying images received from each of the first and second cameras; and
   a medical navigation system for tracking a target object during the surgical procedure,
   wherein the controller of the surgical imaging system is further configured to adjust the surgical imaging system based on tracking of the target object, and
   wherein at least one of the first optical assembly and the second optical assembly further comprises at least one optical filter, the at least one optical filter independently configured for a plurality of different wavelengths, a plurality of different polarizations, and a plurality of different neutral densities, and the at least one optical filter deployed in an optical path by a filter wheel, and
   wherein the at least one optical filter of the first optical assembly is distinct in relation to the at least one optical filter of the second optical assembly.

\* \* \* \* \*